United States Patent

Hynek et al.

Patent Number: 5,497,086
Date of Patent: Mar. 5, 1996

[54] APPARATUS AND METHOD FOR DETERMINING THE DENSITY OF A METAL PLATED POROUS FOAM

[75] Inventors: Paul A. Hynek, Burlington; Vladimir Paserin, Mississauga; John Ambrose, Oakville, all of Canada

[73] Assignee: Inco Limited, Toronto, Canada

[21] Appl. No.: 228,075

[22] Filed: Apr. 15, 1994

[30] Foreign Application Priority Data

Jun. 9, 1993 [CA] Canada ................................. 2098073

[51] Int. Cl.⁶ .................. G01N 27/72; G01R 33/12; G01R 33/00
[52] U.S. Cl. .................. 324/228; 324/226; 324/262; 324/235
[58] Field of Search .................. 324/226, 228, 324/229, 230, 231, 260, 261, 262, 235

[56] References Cited

U.S. PATENT DOCUMENTS

| | | | |
|---|---|---|---|
| 2,721,973 | 10/1955 | Armour | 324/228 |
| 3,153,191 | 10/1964 | Obenschain et al. | 324/128 |
| 4,232,265 | 11/1980 | Smirnov | 324/260 |
| 4,866,383 | 9/1989 | Taliaferro | 324/228 |
| 5,034,690 | 7/1991 | Taliaferro | 324/228 |
| 5,145,716 | 9/1992 | Paserin et al. | 427/55 |

*Primary Examiner*—Walter E. Snow
*Attorney, Agent, or Firm*—Edward A. Steen

[57] ABSTRACT

A sensor for measuring the density of a magnetic porous material such as foam. The sensor includes a load cell connected to a magnet. The magnet is spaced a predetermined distance away from the material. The load sensed by the pull of the magnet is translated into a perceivable density value.

8 Claims, 2 Drawing Sheets

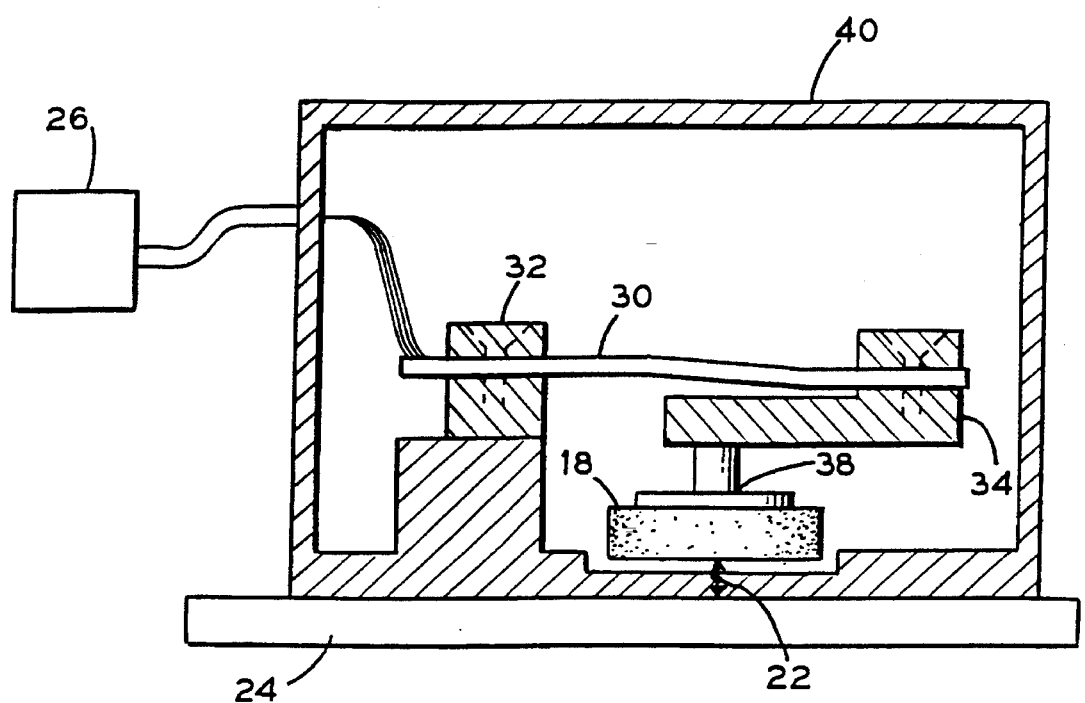

APPARATUS AND METHOD FOR DETERMINING THE DENSITY OF A METAL PLATED POROUS FOAM

TECHNICAL FIELD

The invention relates to the measurement of physical properties in general and, more particularly, to the measurement of the density of metal bearing porous materials such as foams and felts.

BACKGROUND ART

A technique has been developed to plate metal derived from a metal carbonyl gas onto a porous substrate. See U.S. Pat. No. 5,145,716.

In a practical application of the aforementioned technique, nickel is plated into the interstices of a polymeric foam. The treated foam is utilized in nickel cadmium energy cells.

Measuring the amount of deposited nickel per unit area of foam provides critical information for both foam plating process control and quality assurance. In the past, this information was obtained by curing small samples and weighing them on an analytical balance. Some non-destructive measurement methods such as electrical conductivity, light transmission, air pressure drop or infrared absorption were also tried, but with limited success. The measurement accuracy of these techniques was lower than required for acceptable quality control. The main sources of error were in the thickness and pore size variation. With electrical conductivity, the errors were caused by edge effects and density non-uniformity which affected the test current distribution.

A dependable method of determining the mount of nickel per unit area is by using a nuclear density gauge. This technique involves passing rays of beta or gamma radiation through the sample and measuring the amount of transmitted radiation. Such system are commercially available but at a relatively high cost.

The instant invention utilizes a load cell to generate a signal that is translated into a quantifiable density reading.

Load cells have been used to detect the presence of metallic components in products. See, for example, U.S. Pat. Nos. 4,866,383 and 5,034,690. Also, U.S. Pat. No. 4,232,265 senses the relative movement of two plates via the use of a strain gauge. However, the aforementioned patents do not measure the density of magnetic foams.

SUMMARY OF THE INVENTION

Accordingly, there is provided a non-destructive technique for measuring the density of a locally uniform, porous magnetic material.

The ferromagnetic properties of nickel below its Curie point can be used to quantify the amount of nickel or any other metal in a sheet material of relatively uniform density and overall thickness, such as nickel foam. A sensor incorporating a load cell is used to measure the attractive force between a magnet and the metal bearing substrate. Maintaining a fixed proximity between the magnet and substrate, this force is a function of the foam density in the area immediately beneath the magnet.

The sensor can replace a significantly more costly technique of utilizing a nuclear density probe to measure the density of foam.

BRIEF DESCRIPTION OF THE DRAWINGS

FIG. 3 is an elevation of an alternative embodiment of the invention.

PREFERRED MODE FOR CARRYING OUT THE INVENTION

Figure 1:
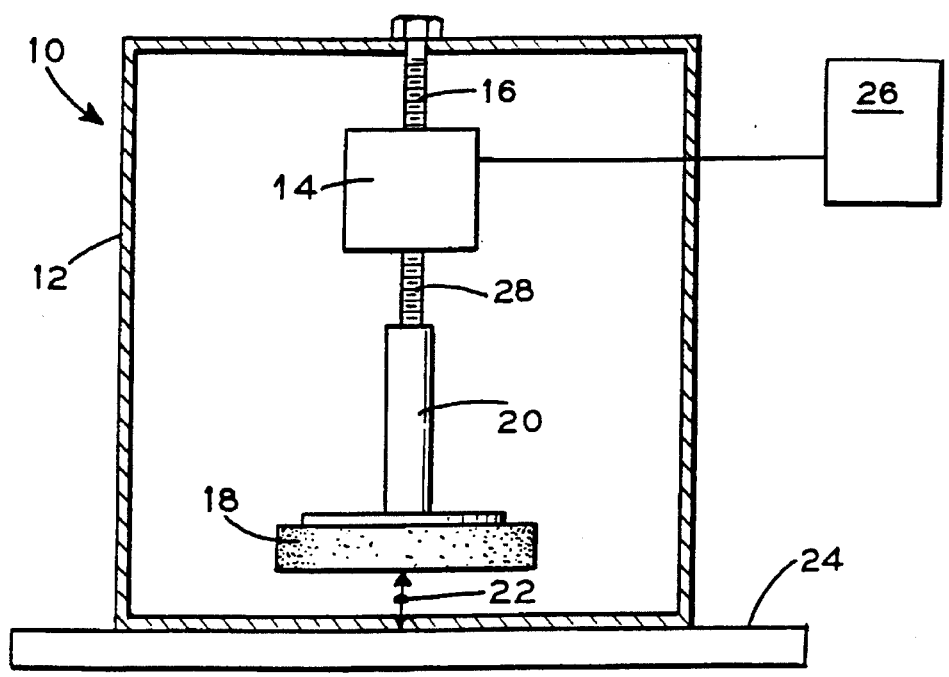
FIG. 1 is an elevation of an embodiment of the invention.

FIG. 1 depicts a sensor 10 for measuring the density of metal foam.

In the ensuing discussion, various dimensions will be given. However, it should be appreciated that these non-limiting numbers are merely examples and are not to be considered as mandatory measurements. Moreover, although the discussion recites nickel coated polymeric foam, it should be clear that the density of any magnetic porous material, plated or otherwise, may be measured.

The sensor 10 preferably includes a non-magnetic housing 12. The housing 12 is placed upon a sample 24. A strain gauge or lead cell 14 is affixed to a support member 16 disposed within the housing 12. A threaded support member 28 extends from the cell 14.

A magnet 18 is positioned below the load cell 14 and is physically registered to it. It is preferred to utilize the threaded support member 28. This allows one to easily position the magnet 18 a fixed distance 22 above the sample 24 to be measured.

Accordingly, the magnet 18 is affixed to a threaded stem 20. By rotating the stem 20 about the support member 28, the vertical distance 22 between the bottom of the magnet 18 and the sample 24 may be modified and fixed as necessary.

In order to protect the interior of the sensor 10 and maintain a relative consistency in the readings, it is preferred to recess the magnet 18 within the housing 12. This can be easily accomplished by sizing the housing 12 to extend beyond the bottom of the magnet 18.

The load cell 14 communicates with an output device 26 which will translate the output of the cell 14 into a perceivable density value. The device 26 may be a process meter, a computer or some other appropriate apparatus.

The invention and manner of applying it may be better understood by a brief discussion of the principles underlying the invention.

In the nickel foam plating process as discussed in U.S. Pat. No. 5,145,716, the amount of nickel deposited on the polyurethane sample or substrate 24 from the plating gas is a function of a number of process conditions, such as gas concentration, substrate temperature, substrate speed, etc. To control these conditions, a real-time feedback signal representing the amount of nickel already deposited on the foam sample 24 is essential for successful process control and for meeting the density and uniformity specifications for the final product.

The load cell 14 must be sufficiently sensitive to provide a useful measurable signal as a function of the foam density. Load cells in the 50–200 g maximum load range are preferable although other ranges are acceptable. The magnet 18 must be of sufficient strength. Rare-earth or cobalt magnets work well. The constant distance 22 between the magnet 18 and the foam surface 24 must be maintained and it must be sufficiently small to produce a measurable force between the two magnetic materials. The area measured by the sensor 10 is approximately the same diameter as the magnet, typically a circle approximately 1–2.5 cm in diameter. A spacing 22 in the order of 1 to 3 mm has been found to be suitable.

A prototype sensor 10 as shown in FIG. 1 was built having a cylindrical plastic housing 12 6.5 cm high and 3.8 cm in diameter. The vertical distance 22 was 2 mm. The extended surface of the housing 12 contacts the nickel foam sample 24 thus maintaining a constant distance between the magnet 18 and the surface of the foam sample 24.

Experimental tests were conducted as follows. A swatch (designated "Test A") of the nickel plated foam 24 was cut and placed underneath the sensor 10. The stem 20 was rotated so as to leave the magnet 18 approximately 2 mm above the sample (Alternatively, the distance between the cell 14 and the magnet 18 can be fixed whereas the height of the housing 12 over the sample 24 is predetermined so as to effect the proper gap 22 between the magnet 18 and the sample 24).

The housing 12 was placed over the stationary sample 24 and the sensor 10 was energized.

The output of the load cell 14 must be calibrated so as to allow the output device 26 to display the density of the sample in an intelligible fashion. The output of the load cell 14 is compared to known standard densities. These values are then correlated to values generated by standard regression analysis techniques. The resultant conversion or correlation factor then modifies the raw output of the load cell 14 to provide a density value.

Tests on the sensor 10 employed a 250 g (2.45N) SENSOTEC™ load cell (model 31). It provided a 21.1 mV signal for zero density (signal due to the mass of the magnet 18 the member 23 and the stem 20) and a 40.8 mV output for 598 g/m² foam (i.e. a net signal of about 20 mV, representing a force of about 0.36N). Other load cells were also evaluated, and a summary of test results is shown in Table 1:

The signal voltages shown in Table 1 were obtained with a single magnet (Neodymium-Iron-Boron or Cobalt), 1.91 cm in diameter, 0.635 cm thick, except for the OMEGA load cell, which was tested with a 1.27 cm diameter, 0.317 cm thick magnet.

Figure 2:
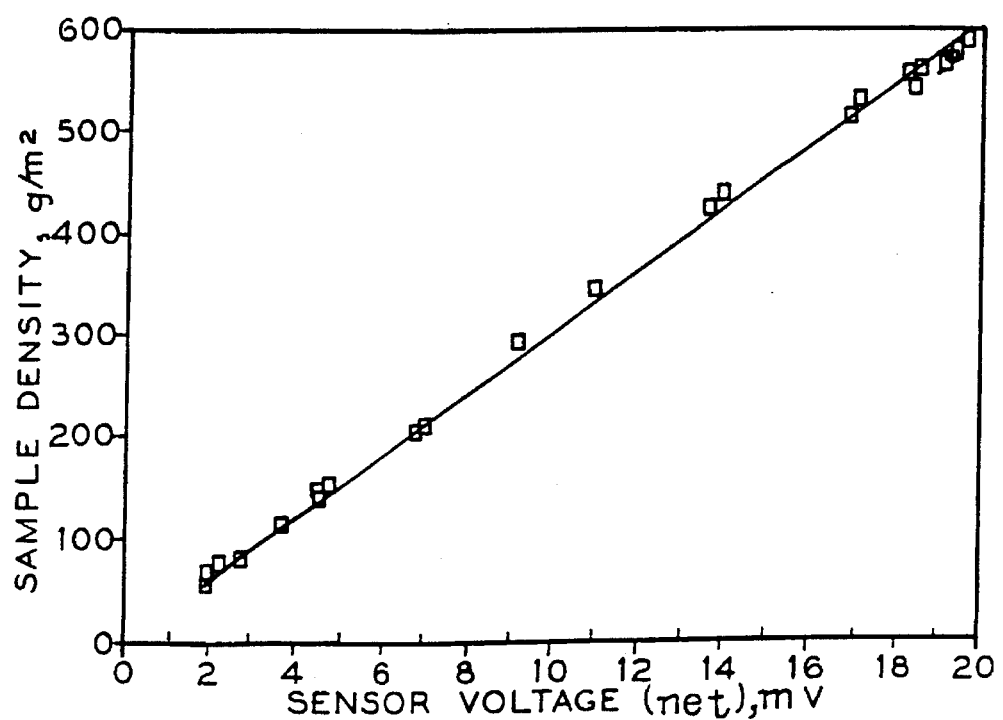
FIG. 2 is a sample calibration curve for the invention.

The calibration data presented in Table 2 and the resulting graph in FIG. 2 were obtained with the two magnets joined together. The linear regression provides an acceptable approximation in this case. The relation is actually non-linear due to the very slight changing distance between the magnet and foam surface for different densities (i.e., higher density leads to higher attractive force which leads to smaller distance). An indication of this fact can be seen in the slight curvature of the discrete points in the graph. □ represents measured data and the resultant line is based upon a zero intercept regression analysis.

The best data available is the calibration data shown in Table 2. This data applies to the SENSOTEC 250 g load cell. The average absolute error estimated from the measurement of samples in the 50–600 g/m² density range was 6.58 g/m², or 2.8% (calculated as the difference between the density measured by sample weighing and that obtained by the magnetic density probe).

TABLE 1

| LOAD CELL | LOAD CELL RANGE | NET SIGNAL FOR 600 g/m² FOAM |
|---|---|---|
| SENSOTEC, Model 31 | 150 g | 22 mV |
| SENSOTEC, Model 31 | 250 g | 20 mV |
| INTERFACE ™, Model MB5 | 2270 g | 0.82 mV |
| INTERFACE, Model SP1 | 1362 g | 1.03 mV |
| OMEGA ™, Model LCL-113 g | 113 g | 2.91 V |

TABLE 2

Calibration Data
2.54 cm diameter samples from Test A (AS-PLATED SAMPLES) were weighed and
magnetic probe voltage readings taken with Keithley ™ multimeter
Sample radius (cm): 1.257 (average of 4 readings)
Zero density sensor voltage (mV): 21.12 (average of 3 readings)

| sample | sensor voltage, mV | | | | mass, g | measured density (by weighing) g/m² | calculated density using intercept regression | absolute error, g/m² | relative error, % |
|---|---|---|---|---|---|---|---|---|---|
| | 1 | 2 | 3 | average net | | | | | |
| 1 | 23.46 | 23.32 | 23.29 | 23.35  2.24 | 0.066 | 72.53 | 67.94 | 4.99 | 6.84 |
| 2 | 23.25 | 23.15 | 23.17 | 23.19  2.07 | 0.063 | 66.89 | 62.99 | 3.91 | 5.85 |
| 3 | 23.14 | 23.12 | 23.14 | 23.13  2.02 | 0.057 | 54.91 | 61.26 | 6.45 | 11.77 |
| 4 | 23.84 | 23.87 | 23.89 | 23.87  2.75 | 0.071 | 83.01 | 83.64 | 0.53 | 0.64 |
| 5 | 24.84 | 24.86 | 24.84 | 24.85  3.73 | 0.087 | 115.23 | 113.30 | 1.93 | 1.67 |
| 6 | 25.88 | 26.71 | 00.00 | 00.00  4.00 | 0.101 | 143.43 | 139.11 | 10.85 | 7.26 |

TABLE 2-continued

Calibration Data
2.54 cm diameter samples from Test A (AS-PLATED SAMPLES) were weighed and
magnetic probe voltage readings taken with Keithley ™ multimeter
Sample radius (cm): 1.257 (average of 4 readings)
Zero density sensor voltage (mV): 21.12 (average of 3 readings)

| sample | sensor voltage, mV | | | | mass, net | g | measured density (by weighing) g/m² | calculated density using intercept regression | absolute error, g/m² | relative error, % |
|---|---|---|---|---|---|---|---|---|---|---|
| | 1 | 2 | 3 | average | | | | | | |
| 7 | 25.68 | 25.69 | 25.64 | 25.68 | 4.55 | 0.101 | 143.43 | 138.11 | 5.32 | 3.71 |
| 8 | 25.72 | 25.70 | 25.69 | 25.70 | 4.59 | 0.100 | 141.42 | 139/33 | 2.09 | 1.48 |
| 9 | 25.87 | 25.81 | 25.83 | 25.84 | 4.72 | 0.106 | 153.50 | 143.38 | 10.12 | 6.59 |
| 10 | 28.00 | 28.04 | 28.11 | 28.05 | 6.93 | 0.134 | 209.90 | 210.61 | 0.71 | 0.34 |
| 11 | 30.62 | 30.36 | 30.48 | 30.49 | 9.37 | 0.175 | 292.48 | 294.63 | 7.85 | 2.68 |
| 12 | 32.33 | 32.33 | 32.41 | 32.36 | 11.24 | 0.2M | 348.87 | 341.43 | 7.44 | 2.13 |
| 13 | 35.10 | 34.95 | 35.07 | 35.04 | 13.92 | 0.248 | 439.51 | 422.94 | 16.57 | 3.77 |
| 14 | 38.19 | 38.25 | 39.14 | 38.19 | 17.07 | 0.293 | 530.15 | 518.63 | 11.52 | 2.17 |
| 15 | 30.64 | 39.49 | 39.41 | 39.51 | 18.39 | 0.310 | 564.39 | 599.73 | 5.66 | 1.00 |
| 16 | 40.60 | 40.57 | 40.46 | 40.54 | 19.43 | 0.319 | 592.52 | 690.12 | 7.60 | 1.30 |
| 17 | 39.70 | 39.72 | 39.68 | 39.70 | 18.59 | 0.308 | 560.36 | 594.50 | 4.14 | 0.74 |
| 18 | 39.77 | 39.50 | 39.27 | 39.51 | 19.40 | 0.301 | 546.26 | 558.93 | 12.57 | 2.30 |
| 19 | 39.79 | 39.71 | 39.59 | 39.70 | 19.55 | 0.310 | 564.39 | 564.50 | 0.01 | 0.00 |
| 20 | 34.83 | 34.92 | 34.96 | 34.90 | 13.79 | 0.242 | 427.43 | 418.79 | 8.63 | 2.02 |
| 21 | 38.06 | 37.99 | 38.04 | 38.03 | 16.91 | 0.286 | 516.06 | 513.77 | 2.29 | 0.44 |
| 22 | 39.47 | 39.31 | 39.41 | 39.40 | 18.28 | 0.307 | 558.35 | 555.28 | 3.06 | 0.55 |
| 23 | 40.85 | 40.75 | 40.85 | 40.82 | 19.70 | 0.324 | 592.59 | 598.42 | 5.83 | 0.96 |
| 24 | 40.44 | 40.34 | 40.30 | 40.36 | 19.24 | 0.314 | ⁻572.45 | 584.55 | 12.10 | 2.11 |
| 25 | 40.37 | 40.33 | 40.31 | 40.24 | 19.12 | 0.312 | 558.42 | 590.90 | 12.38 | 2.18 |
| | | | | average errors (full density range): | | | | | 6.58 | 2.82 |
| | | | | average errors (200–600 g/m² density range): | | | | | 7.40 | 1.55 |

The readings from the load cell 14 can be directed to the output device 26. A computer screen may display the values if the signal is interfaced to the computer via a signal conditioning module. Alternatively, a process meter (such as a Omega™ DM-41) can be used. The meter can be easily calibrated using the 2-point calibration method.

Still another way to obtain the density values is to use an accurate voltmeter and calculate the densities using a calibration equation derived from the regression analysis.

FIG. 3 discloses a preferred alternative embodiment of the invention. Actually, the device shown in FIG. 1 worked well as a prototype but due to cost considerations it was redesigned using an OMEGA LC series thin beam load cell 30.

The thin beam load cell 30 includes supports 32 and 34. The magnet 18 is affixed to the support 34 via a disc and block 38. The components are disposed in a housing 40. The magnet 18 and load cell 30 are enclosed in the housing 40 to prevent contamination and to protect the mechanism. In addition, the housing 40 maintains the vertical distance 22 constant.

The electrical connection end of the thin beam load cell 30 is fixed to the housing 40. The magnet 18 is attached to the support 34 so as to suspend the magnet 18 under the midpoint of the beam 30. Thus, when there is an attractive force on the magnet 18, the beam distorts into a double bend. A strain gauge on the beam 30 generates an electrical output to the device 26 proportional to the combined tension and compression on the beam 30.

From a practical standpoint, the selection of the load cell 14 and 30 is a controlling cost factor. Commercial load cells 14 and 30 vary in their output. A lower net signal output (see Table 1) requires increased vigilance in measuring and processing the signal. Higher output cells generally cost more. Accordingly, economic considerations must be factored into the construction equation.

While in accordance with the provisions of the statute, there is illustrated and described herein specific embodiments of the invention, those skilled in the art will understand that changes may be made in the form of the invention covered by the claim and that certain features of the invention may sometimes be used to advantage without a corresponding use of the other features.

The embodiments of the invention in which an exclusive property or privilege is claimed are defined as follows:

1. An apparatus for measuring the density of a metal plated porous foam sample, the apparatus comprising a magnet, the magnet connected to a load cell, means for maintaining the magnet a fixed distance away from the sample, the load cell adapted to produce an output signal that is a function of the density of the sample, and the output signal of the load cell connected to a density display device.

2. The apparatus according to claim 1 disposed within a housing having a bottom, and the housing bottom extending beyond the magnet so as to space the magnet from the sample.

3. The apparatus according to claim 1 wherein the load cell is a thin beam load cell.

4. The apparatus according to claim 2 wherein the load cell is a thin beam load cell, the thin beam load cell is supported by the housing.

5. The apparatus according to claim 2 wherein a first stem is disposed within the housing, the load cell is affixed to the first stem, the magnet is connected to the load cell, and the magnet adapted to be spaced away from the sample.

6. The apparatus according to claim 5 wherein the magnet is threadably affixed to a second stem extending from the load cell.

7. The apparatus according to claim 1 wherein the apparatus is disposed on a nickel plated porous foam sample.

8. A method for determining the density of a metal plated porous foam material including:

a) placing a magnet a fixed distance away from the material;

b) measuring the force experience by the magnet vis-a-vis the material by a load cell; and c) translating the resultant force into a density value of the foam.

* * * * *